United States Patent
Hwang et al.

(10) Patent No.: US 6,471,651 B1
(45) Date of Patent: Oct. 29, 2002

(54) LOW POWER PORTABLE ULTRASONIC DIAGNOSTIC INSTRUMENT

(75) Inventors: Juin-Jet Hwang, Mercer Island; Justin M. Coughlin, Seattle; Davin Dhatt, Woodinville; Geoffrey Jones, Seattle; Blake W. Little, Bothell, all of WA (US)

(73) Assignee: SonoSite, Inc., Bothell, WA (US)

( * ) Notice: Subject to any disclaimer, the term of this patent is extended or adjusted under 35 U.S.C. 154(b) by 0 days.

(21) Appl. No.: 09/564,299

(22) Filed: May 3, 2000

Related U.S. Application Data

(60) Provisional application No. 60/132,558, filed on May 5, 1999.

(51) Int. Cl.[7] .................................................. A61B 8/00
(52) U.S. Cl. ........................ 600/459; 600/443; 600/437
(58) Field of Search ................................. 600/459, 442, 600/455, 456, 457, 443, 444, 460, 447

(56) References Cited

U.S. PATENT DOCUMENTS

| | | | |
|---|---|---|---|
| 5,795,297 A | * 8/1998 | Daigle | 600/447 |
| 5,817,024 A | 10/1998 | Ogle et al. | 600/447 |
| 5,865,749 A | 2/1999 | Doten et al. | 600/443 |
| 5,964,709 A | * 10/1999 | Chaing et al. | 600/447 |
| 6,117,085 A | * 9/2000 | Picatti | 600/459 |
| 6,135,961 A | * 10/2000 | Pflugrath et al. | 600/447 |

* cited by examiner

*Primary Examiner*—Francis J. Jaworski
*Assistant Examiner*—Maulin Patel
(74) *Attorney, Agent, or Firm*—Townsend and Townsend and Crew LLP; Henry K. Woodward

(57) ABSTRACT

A portable ultrasonic diagnostic instrument including an array transducer, a beamformer, signal processing and imaging circuitry, and a display for the processed echo signals operates on no more than 25 watts of electrical power. Circuit functions can be selecting attend depending on mode of operation of the instrument to thereby reduce power consumption. Further, a power monitor and control can monitor electrical current from a battery power source, and when power consumption reaches a pre-determined level the power monitor and control further alters one or more functional units in the instrument including display mode of operation, clock frequency for analog to digital conversion and signal processing, color signal processing, and 3D signal processing. Power consumption can be monitored against two or more pre-determined levels wherein instrument functional units or mode of operation are altered depending on which level of power consumption has been reached. In an instrument with an analog beamformer power consumption can be limited to 10 watts, whereas in a digital beamformer instrument power consumption can be limited to no more than 25 watts.

26 Claims, 2 Drawing Sheets

LOW POWER PORTABLE ULTRASONIC DIAGNOSTIC INSTRUMENT

This patent application claims the benefit of Provisional Patent Application Serial No. 60/132,558, filed May 5, 1999.

BACKGROUND OF THE INVENTION

This invention relates generally to medical ultrasonic diagnostic systems, and more particularly the invention relates to a portable ultrasonic diagnostic instrument which operates at low power.

Modern ultrasonic diagnostic systems are large, complex instruments. Today's premium ultrasound systems, while mounted in carts for portability, continue to weigh several hundred pounds. In the past, ultrasound systems such as the ADR 4000 ultrasound system produced by Advanced Technology Laboratories, Inc., were smaller desktop units about the size of a personal computer. However, such instruments lacked many of the advanced features of today's premium ultrasound systems such as color Doppler imaging and three dimensional display capabilities. As ultrasound systems have become more sophisticated they have also become bulkier.

Disclosed in U.S. Pat. No. 5,722,412 is a diagnostic ultrasound instrument which exhibits many of the features of a premium ultrasound system in a hand-held unit. The instrument can be produced as a single unit or, in a preferred embodiment, the instrument is a two part unit one including a transducer beamformer an image processor and the other including a display and power source for both units. In such a configuration the transducer/processor unit can be manipulated with one hand while a cable between the two units enables the video to be shown on the display unit while the latter unit is held or positioned for optimal viewing of the ultrasound image. The cable also provides energy for the transducer/processor unit from the display.

In a preferred embodiment the ultrasound system from the transducer to the video output is fabricated on four types of application specific integrated circuits (ASICs): a transmit/receive ASIC which is connected to the elements of an array transducer, a front end ASIC which performs and controls transmit and receive beamforming, a digital signal processing ASIC which provides processing of the ultrasound signals such as filtering, and a back end ASIC which receives processed ultrasound signals and produces ultrasound image data. The image can be displayed on either a standard monitor or on a liquid crystal display (LCD). The elements of the unit including the ASIC can be fabricated on a single printed circuit board, thus eliminating the problems conventionally posed by connectors and cables. This sophisticated ultrasound instrument can be manufactured as a hand held unit weighing less than five pounds.

A limiting factor in portable ultrasonic diagnostic instruments is the power required for operation. Typically at least 35 watts of power are required for digital beamforming instrument whereas an analog beamforming instrument requires a minimum of 15 watts of power. The digital beamformer is more precise in performance, but the analog to digital and digital to analog signal conversions require considerably more power than the analog beamformer which requires no conversion and relies on phase modulation in beamforming.

The present invention is directed to providing a portable ultrasonic diagnostic instrument, either digital, analog or hybrid, with reduced power in operation.

SUMMARY OF THE INVENTION

In accordance with the invention a portable ultrasonic diagnostic instrument is provided which includes an array transducer, a beamformer for delaying and combining echo signals received by elements of the array transducer, signal processing and imaging circuitry for processing the echo signals, and a display for the processed echo signals, wherein the instrument operates on no more than 25 watts of electrical power. In one embodiment with an analog beamformer, the instrument operates on no more than 10 watts of power.

More particularly, the portable ultrasonic diagnostic instrument operates from battery power, and power control is provided for limiting power consumption in the instrument to 25 watts for a digital beamformer instrument or 10 watts for an analog beamformer instrument. Before operation of the instrument, various modes of operation are evaluated for required circuit functions, and other circuit functions are powered down or turned-off to conserve power. For example, B mode scanning does not require color power angiography and this function is turned-off. Similarly, sampling at a lower rate allows the analog to digital function to operate at a lower frequency thus reducing power consumption. In a sleep mode, the monitor display intensity can be diminished. Further, during operation of the instrument current from the battery source to the instrument components is monitored, and when the current reaches a first selected power limit, first functions in the instrument are altered to thereby reduce power consumption. For example, function can be the display of processed signals, and the display can be shifted in mode from active scanning to a mode selected from freeze and sleep which require less power. Additionally, un-needed functional blocks such as color display and 3D display of processed signals can be turned off. In a digital beamformer instrument, considerable power is expended in the analog to digital conversion of signals from the ultrasound transducers, and power can be conserved by reducing the clock frequency to the analog to digital converters. Similarly, the clock frequency to the digital signal processor of the instrument can reduced with attendant power savings. Thus, power reduction can be effected before instrument operation and/or during operation.

In an alternative embodiment, current from the battery source is monitored during instrument operation and first functions in the instrument operation are altered when the power consumption has reached a first power limit, and additional functions when monitored current reaches a second power limit whereby instrument operation is altered in steps. An ultimate threshold can be reached wherein the instrument operation is terminated entirely until troubleshooting of the instrument for possible failure is completed.

The invention and objects and features thereof will be more readily apparent from the following detailed description and appended claims when taken with the drawings.

DETAILED DESCRIPTION OF ILLUSTRATIVE EMBODIMENTS

Figure 1:
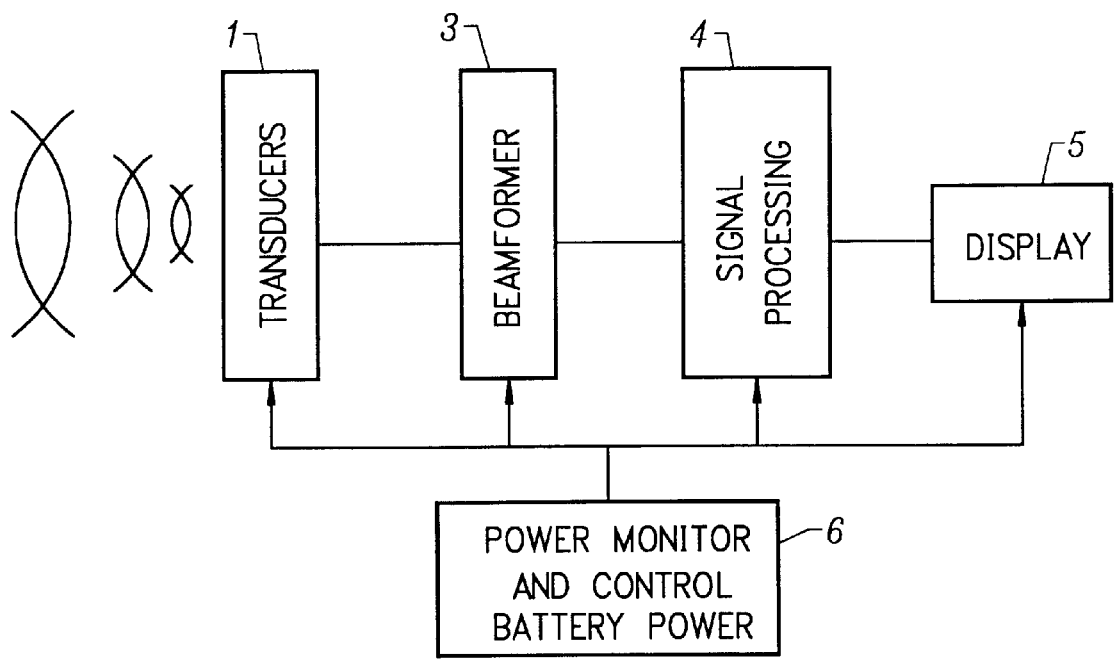
FIG. 1 is a functional block diagram of a portable ultrasonic diagnostic instrument including a power monitor and control in accordance with the invention.

FIG. 1 is a functional block diagram of a portable ultrasonic diagnostic instrument in which the present invention is employed. Ultrasound transducers 1 generate ultrasonic waves shown generally at 2 and receive reflections of the ultrasonic waves. Wave generation and echo signal processing is accomplished by a beamformer circuit 3 which interfaces with the transducers 1. Signals from beamformer 3 are then passed to a signal processor 4, and the process signals are then used to control a display 5. Electric power for the components of the instrument provided by a battery source 6 which includes a power monitor and control in accordance with the present invention.

Heretofore, portable ultrasonic diagnostic instruments have been available but have operated at power levels exceeding 35 watts. The present invention limits power consumption to 25 watts for a digital beamformer instrument and 10 watts for an analog beamformer instrument. The analog beamformer instrument has improved fidelity when compared with the analog beamformer, but the analog to digital conversion circuits and amplifiers require considerably more power than does an analog beamformer. For example, a transducer array with 100 elements and analog to digital circuits can expand 64 milliwatts per element or 6.4 watts total just for the analog to digital conversion.

Additionally, a time gain control (TGC) amplifier also expends approximately 64 milliwatts per transducer which is an additional 6.4 watts.

In accordance with the invention, selected circuit functions are powered down or turned-off depending on. the operating mode of the instrument. For example, for B mode scanning, the Color Power Angio circuitry is turned-off. For Scan/Transmit without Wide Aperture, the Synthetic Aperture function is not needed and is turned-off. Similarly, if a rough image is sufficient during an operating mode, the Frequency Compounding function is not needed. Two dimensional (2D) mode of operation does not require any 3D processing. Low frequency cardiac imaging permits a reduction in Front End (FE) clock frequency and possibly a reduced frequency for the entire signal path. Analog to Digital conversion speed can be reduced and thus save power when data sampling frequency is reduced.

Accordingly, power is saved by selective use of instrument circuitry depending on mode of operation of the instrument.

Figure 2:
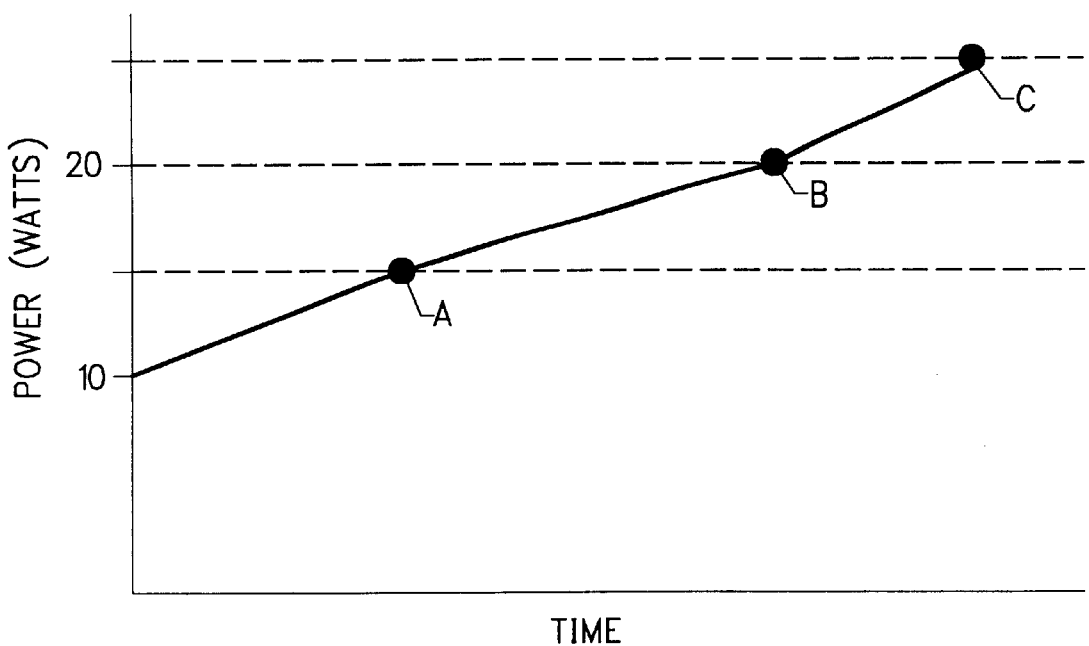
FIG. 2 is a graphic illustrating operation of the power monitor in FIG. 1.

FIG. 2 is a graph illustrating operation of the power monitor and control in power source 6 of FIG. 1. The graph illustrates power along the coordinate and time along the abscissa. In this example it is assumed that power consumption is to be limited to 1520 watts during normal operation and in no event exceed 25 watts of power. A first power limit is defined at 15 watts, a second power limit is defined at 20 watts, and a third power limit is defined at 25 watts. Assume that during instrument operation power consumption rises from 10 watts to 15 watts at Point A on the graph. In accordance with one embodiment of the invention the power monitor and control 6 in FIG. 1 alters first functions in the instruments, as described above, and additionally during operation. For example, when the power reaches Point A (15 watts) function and operating speed can be further reduced in order to reduce power consumption. The first functions can include mode of operation of display 5 with the display switched from active scanning to a freeze mode. Since the display is one of the larger consumers of electrical power, the switch of display mode can limit further increase in power consumption. However, assuming power consumption continues to rise from 15 watts (Point A) to 20 watts (Point B), the power monitor and control will then alter second functions in the instrument operation to further limit power consumption. These alterations can include reducing clock frequency to the digital signal processor and clock frequency to analog to digital circuitry in the beamformer.

Figure 3:
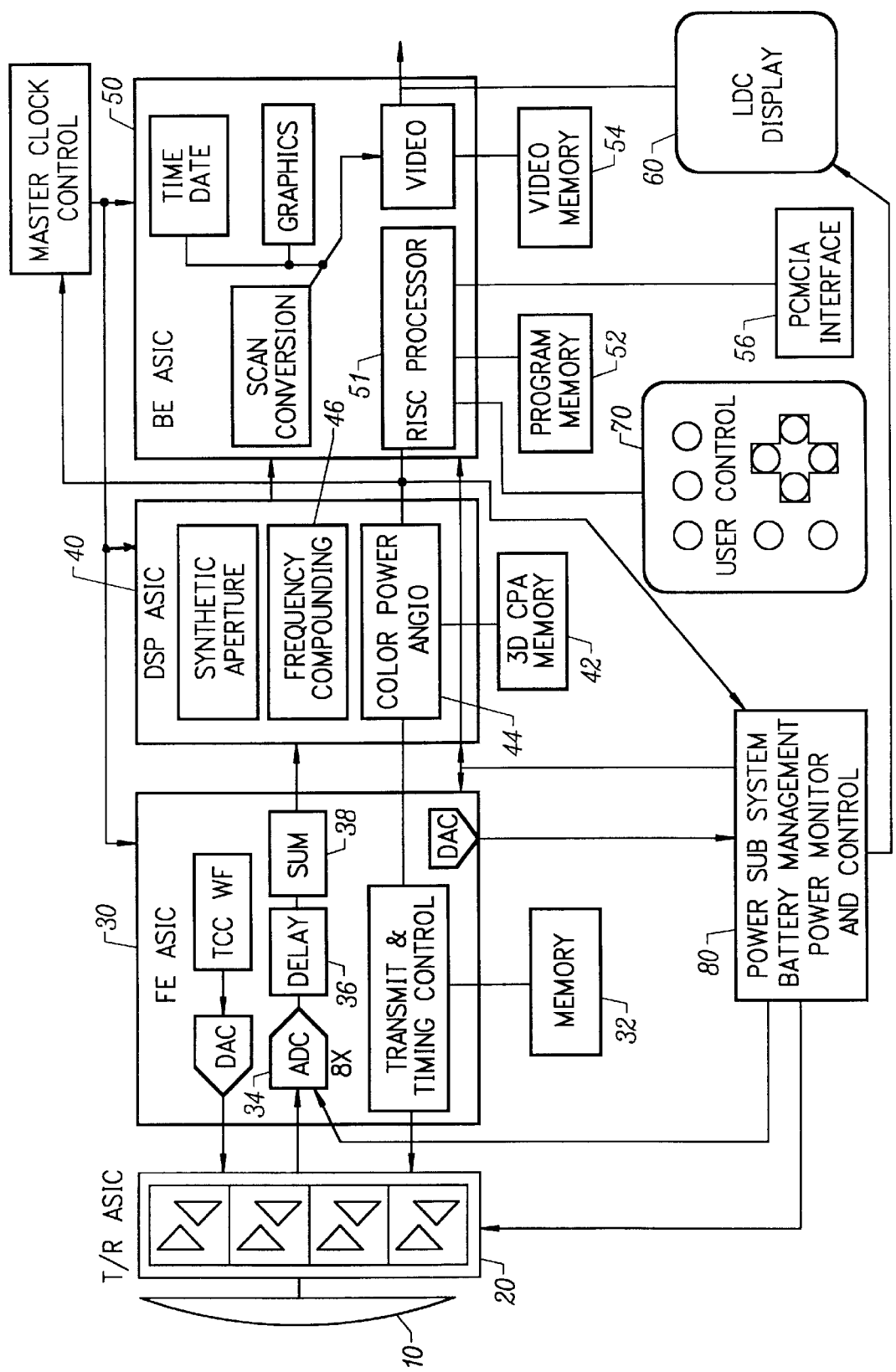
FIG. 3 is a more detailed functional block diagram of a ultrasonic diagnostic instrument having a digital beamformer and a power monitor in accordance with the invention.

FIG. 3 is a more detailed functional block diagram of a ultrasonic diagnostic instrument having a digital beamform and further illustrates functions in the instrument which can be altered by the power monitor and control. The instrument is described in more detail in U.S. Pat. No. 5,722,412, which is incorporated herein by reference. In this instrument a transducer array 10 is used for a solid state, electronic control capabilities, variable aperture, image performance and reliability. Either a flat or curved linear array can b e used. In a preferred embodiment the array is a curved array, which affords a broad sector scanning field. While the preferred embodiment provides sufficient delay capability to both steer and focus a flat array such as a phased array, the geometric curvature of the curved array reduces the delay requirements on the beamformer. The elements of the array are connected to a transmit/receive ASIC 20 which drives the transducer elements and receives echoes received by the elements. The transmit/receive ASIC 30 also controls the transmit and receive apertures of the array 10 and the gain of the received echo signals. The transmit/receive ASIC is preferably located within inches of the transducer elements, preferably in the same enclosure, and just behind the transducer.

Echoes received by the transmit/receive ASIC 20 are provided to the adjacent front end ASIC 30, which beamforms the echoes from the individual transducer elements into scanline signals. The front end ASIC 30 also controls the transmit waveform, timing, aperture and focusing. In the illustrated embodiment the front end ASIC 30 provides timing signals for the other ASICs, time gain control, and monitors and controls the power applied to the transducer array, thereby controlling the acoustic energy which is applied to the patient and minimizing power consumption of the unit. A memory device 32 is connected to the front end ASIC 30, which stores data used by the beamformer.

Beamformer scanline signals are coupled from the front end ASIC 30 to the adjacent digital signal processing ASIC 40. The digital signal processing ASIC 40 filters the scanline signals and in the preferred embodiment also provides several advanced features including synthetic aperture formation, frequency compounding. Doppler processing such as power Doppler (color power angio) processing, and speckle reduction.

The ultrasound B mode and Doppler information is then coupled to the adjacent back end ASIC 50 for scan conversion and the production of video output signals. A memory device 42 is coupled to the back end ASIC 50 to provide storage used in three dimensional power Doppler (3D CPA) imaging. The back end ASIC also adds alphanumeric information to the display such as the time, date, and patient identification. A graphics processor overlays the ultrasound image with information such as depth and focus markers and cursors. Frames of ultrasonic images are stored in a video memory 54 coupled to the back end ASIC 50, enabling them to be recalled and replayed in a live Cineloop® realtime sequence. Video information is available at a video output in several formats, including NTSC and PAL television formats and RGB drive signals for an LCD display 60 or a video monitor.

The back end ASIC 50 also includes the central processor for the ultrasound system, a RISC (reduced instruction set controller) processor. The RISC processor is coupled to the front end and digital signal processing ASICs to control and synchronize the processing and control functions throughout the hand-held unit. A program memory 52 is coupled to the back end ASIC 50 to store program data which is used by the RISC processor to operate and control the unit. The back end ASIC 50 is also coupled to a data port configured as a PCMCIA interface 56, This interface allows other modules and functions to be attached to the hand-held ultrasound unit. The interface 56 can connect to a modem or communications link to transmit and receive ultrasound information from remote locations. The interface can accept other data storage devices to add new functionality to the unit, such as an ultrasound information analysis package.

The RISC processor is also coupled to the user controls 70 of the unit to accept user inputs to direct and control the operations of the hand-held ultrasound system.

Power for the hand-held ultrasound system in a preferred embodiment is provided by a rechargeable battery. Battery power is conserved and applied to the components of the unit from a power subsystem 80. The power subsystem 80 includes a DC converter to convert the low battery voltage to a higher voltage which is applied to the transmit/receive ASIC 20 to drive the elements of the transducer array 10.

The power monitor and control in unit 80 operates in accordance with the description with reference to FIG. 2 and controls the operating mode of the LCD display 60 and video circuitry in unit 50 along with the clock frequency of the RISC processor in unit 50 and the clock frequencies of the VCA and ADC units in beamformer circuitry 30. The color power and geography function unit and 3D signal processing of DSP unit 40 are similarly controlled by the power monitor and control.

In FIG. 3, power consumption is controlled by power monitor and control block 80 and master clock control 90 which are both controlled by the RISC processor in block 50. The overall signal path depicted in FIG. 3 contains various functional blocks such as the analog to digital converters (ADC) 34 in block 30, the color power angio processor 44 in block 40, and the frequency compounding processor 46 in block 40. Each such functional block may be turned off individually by the power monitor and control circuit 80. As an example, when the ultrasound system is imaging in B-mode only, the color power angio block 44 is not needed and is turned off.

In addition to controlling whether functional blocks are on or off, power monitor and control block 80 controls the bias current supplied to ADC block 34. Lower frequency operation typically requires less bias current. Similarly, voltage and current supplied to transmit/receive block 20 is controlled as appropriate. As an example, superficial imaging typically will require less transmitted power than deep abdominal imaging.

Power monitor and control block 80 also controls power to LCD display 60, and in particular to the backlight associated with the LCD display. The display may be provided with less current (dimmed) to conserve power.

In terms of overall system operation, the system may be in one of several power conservation modes at any particular time. For example, a full operation mode may draw the most power, while a "freeze" mode that allows review of stored images but not active scanning would draw less power. A sleep mode where the display and most other functions are disabled would draw even less power, while a power-off mode would draw no power. Power monitor and control block 80 controls transitions between these states based on algorithms executed by the RISC processor contained in block 50.

In the preferred embodiment, many of the functional blocks described are embedded in Application Specific Integrated circuits (ASICs) 20,30, 40, and 50 in FIG. 1. The choice of which functions to integrate on each ASIC relates to power consumption. For example, the integration of ADC blocks 34 and delay and sum blocks 36 and 38 are integrated in the same ASIC to conserve power. Separation of these elements would require higher current driver circuitry for communication between blocks.

The use of power monitor and control functions in a portable ultrasonic diagnostic instrument limits power consumption and enables an instrument operating within a limited power range. While the invention has been described with reference to specific embodiments the description illustrative of the invention and is not to be construed as limiting the invention. Various modifications and applications may occur to those skilled in the art without departing from the true spirit and scope of the invention as defined by the appended claims.

What is claimed is:

1. In a portable ultrasonic diagnostic instrument having ultrasound transducers for transmitting and receiving ultrasonic waves and beamforming circuitry for focusing transmitted and received waves, a method of operating the instrument at a reduced power consumption level comprising the steps of:
   a) providing a battery source of electrical current for circuitry in the instrument, and
   b) selectively altering circuitry functions depending on mode of operation of the instrument when a first power limit is reached, thereby reducing power consumption.

2. The method as defined by claim 1 wherein step b) is performed before instrument operation.

3. The method as defined by claim 2 wherein step b) is performed also during instrument operation.

4. The method as defined by claim 2 wherein the instrument further includes signal processing circuitry, imaging circuitry for controlling a display of processed signals, and a display.

5. The method as defined by claim 4 wherein step b) includes altering display of processed signals.

6. The method as defined by claim 5 wherein the display of processed signals is shifted in mode from active scanning to a mode selected from freeze and sleep.

7. The method as defined by claim 4 wherein step b) further includes turning off un-needed functional blocks.

8. The method as defined by claim 7 wherein un-needed functional blocks includes color display and 3D display of processed signals.

9. The method as defined by claim 4 wherein step b) further includes reducing clock frequency for at least one functional unit.

10. The method as defined by claim 9 wherein the at least one functional unit includes analog to digital signal conversion.

11. The method as defined by claim 9 wherein the at least one functional unit includes a data processor.

12. The method as defined by claim 1 wherein step b) further includes altering second functions in instrument operation when monitored current indicates the power consumption has reached a second power limit.

13. The method as defined by claim 12 wherein first functions and second functions selected from display operation, color signal processing, 3D signal processing, clock frequency for analog to digital signal conversion, and clock frequency for data processing.

14. A portable ultrasonic diagnostic instrument comprising:

a) ultrasound transducers for transmitting and receiving ultrasonic waves, b) beamforming circuitry for focusing transmitted and received waves, c) a display, f) battery power, and d) power control for limiting power consumption in the instrument not to exceed 25 watts.

15. The portable ultrasonic diagnostic instrument as defined by claim 14 wherein the beamforming circuitry is digital.

16. The portable ultrasonic diagnostic instrument as defined by claim 15 wherein the power control reduces clock frequency to analog to digital converter circuitry in the beamformer when power consumption exceeds a first limit.

17. The portable ultrasonic diagnostic instrument as defined by claim 16 and further including:

e) signal processing circuitry for processing electrical signals from received waves, f) imaging circuitry for controlling a display of processed signals, and g) a display.

18. The portable ultrasonic diagnostic instrument as defined by claim 14 wherein the power control blocks color display and 3D display of processed signals.

19. The portable ultrasonic diagnostic instrument as defined b claim 18 wherein power control alters display of processed signals.

20. The portable ultrasonic diagnostic instrument as defined by claim 19 wherein the display of processed signals is shifted in mode from active scanning to a mode selected from freeze and sleep.

21. The portable ultrasonic diagnostic instrument as defined by claim 14 wherein the beamforming circuitry is analog and the power control limits power consumption to 10 watts.

22. The portable ultrasonic diagnostic instrument as defined by claim 21 wherein power control limits one or more functions when power consumption reaches a first level.

23. The portable ultrasonic diagnostic instrument as defined by claim 22 wherein the one or more functions include display operation, color signal processing, 3D signal processing, clock frequency for analog to digital conversion, and clock frequency for data processing.

24. A portable ultrasonic diagnostic instrument comprising:

an array transducer, a beamformer for delaying and combining echo signals received by elements of the array transducer, signal processing and imaging circuitry for processing the echo signals, and a display for the processed signals, wherein the instrument operates on no more than 25 watts of electrical power.

25. The instrument as defined by claim 24 wherein the beamformer is digital.

26. The instrument as defined by claim 24 wherein the beamformer is analog, wherein the instrument operates on no more than 10 nwatts of electrical power.

* * * * *